United States Patent
Giori et al.

(10) Patent No.: US 9,504,270 B2
(45) Date of Patent: Nov. 29, 2016

(54) PROCESS FOR REMOVING PESTICIDES FROM GINKGO BILOBA EXTRACTS, AND EXTRACTS OBTAINABLE BY SAID PROCESS

(75) Inventors: Andrea Giori, Milan (IT); Giacomo Mombelli, Milan (IT); Sabrina Arpini, Milan (IT); Mario Acerbi, Milan (IT)

(73) Assignee: INDENA S.P.A., Milan (IT)

( * ) Notice: Subject to any disclaimer, the term of this patent is extended or adjusted under 35 U.S.C. 154(b) by 1277 days.

(21) Appl. No.: 13/258,715

(22) PCT Filed: Mar. 31, 2010

(86) PCT No.: PCT/EP2010/002046
§ 371 (c)(1),
(2), (4) Date: Nov. 18, 2011

(87) PCT Pub. No.: WO2010/115566
PCT Pub. Date: Oct. 14, 2010

(65) Prior Publication Data
US 2012/0100232 A1    Apr. 26, 2012

(30) Foreign Application Priority Data
Apr. 6, 2009 (IT) .............................. MI2009A0548

(51) Int. Cl.
*A61K 36/16* (2006.01)
*A23L 1/015* (2006.01)

(52) U.S. Cl.
CPC .............. *A23L 1/0152* (2013.01); *A61K 36/16* (2013.01)

(58) Field of Classification Search
None
See application file for complete search history.

(56) References Cited

U.S. PATENT DOCUMENTS

| | | |
|---|---|---|
| 4,753,929 A | 6/1988 | Matsumoto et al. |
| 5,399,348 A | 3/1995 | Schwabe |
| 5,660,832 A * | 8/1997 | Steiner et al. ................ 424/752 |
| 6,174,531 B1 * | 1/2001 | Zhang et al. ................ 424/752 |
| 6,187,314 B1 | 2/2001 | Xie et al. |

FOREIGN PATENT DOCUMENTS

| | | |
|---|---|---|
| EP | 0 360 556 A1 | 3/1990 |
| EP | 0 431 535 A1 | 6/1991 |
| EP | 436129 A1 * | 7/1991 |
| WO | 00/23090 A1 | 4/2000 |
| WO | 2006/009373 A1 | 1/2006 |
| WO | 2006/117170 A1 | 11/2006 |
| WO | WO 2007/126264 A1 * | 4/2007 |

OTHER PUBLICATIONS

Database EPODOC [Online] European Patent Office, The Hague, NL; Nov. 21, 2001, XP002607269, Database Accession No. CN1322723A.
Notification of Transmittal of the International Search Report and the Written Opinion of the Interantional Searching Athority, or the Delcaration Dated Nov. 10, 2010 Issued in PCT/EP2010/002046.

* cited by examiner

*Primary Examiner* — Amy L Clark
*Assistant Examiner* — Catheryne Chen
(74) *Attorney, Agent, or Firm* — Silvia Salvadori, P.C.; Silvia Salvadori

(57) ABSTRACT

Process for removing pesticides from *Ginkgo biloba* extracts, which involves submitting an extract obtained by conventional methods to the following steps:
  a. Liquid-liquid extraction of the extract to obtain a medium polarity fraction containing *ginkgo* terpenes and pesticides not removable with hexane, and a high polarity fraction containing *ginkgo* flavone glycosides;
  b. crystallization from the medium polarity fraction obtained at step a) to give an intermediate with a ginkgolide content of not less than 50%;
  c. crystallization from the residual solution obtained at step b) to give an intermediate with a bilobalide content of not less than 50%;
  d. mixing of the high polarity fraction obtained at step a) with the *ginkgo* terpene intermediate and the bilobalide intermediate obtained at steps b) and c).

2 Claims, No Drawings

PROCESS FOR REMOVING PESTICIDES FROM GINKGO BILOBA EXTRACTS, AND EXTRACTS OBTAINABLE BY SAID PROCESS

This application is a U.S. national stage of PCT/EP2010/002046 filed on Mar. 31, 2010 which claims priority to and the benefit of Italian Application No. MI2009A000548 filed on Apr. 6, 2009, the contents of which are incorporated herein by reference.

The present invention relates to a process for removing pesticides from *Ginkgo biloba* extracts, and the extracts obtainable by said process.

PRIOR ART

*Ginkgo biloba* leaf extracts have long been used in Chinese traditional medicine and in numerous Western countries due to the multiple pharmacological properties attributed to the components of said extracts (vasodilating, immunostimulating, antioxidant and antiaggregant properties).

Processes for the preparation of *Ginkgo biloba* leaf extracts are disclosed in U.S. Pat. No. 5,700,468, EP 360 556, EP 431 535 and JP 09110713.

Pesticides such as organophosphates, the toxicity of which is well documented, have been employed in the cultivation of the plants used to produce said extracts, especially in the past. Although many health and agricultural authorities have banned or restricted the use of such pesticides, it is not always easy to establish the origin of plant material, and even in countries where the use of pesticides is regulated, it is impossible to rule out unlawful or improper use of substances with pesticidal action, whose presence in the pharmaceutical or nutritional grade extract is wholly undesirable. A particularly insidious problem is possible cross-contamination from pesticides originating from nearby crops.

The problem of contamination in general is discussed in the Journal of AOAC International, Vol. 88(3), 2005, 729-735, which also describes a method for the determination of the organophosphate pesticide content of *Ginkgo* leaves by gas chromatography.

U.S. Pat. No. 5,660,832 discloses a general process for purifying plant extracts of pesticides, comprising extraction with a polar solvent in a specific pH range, followed by absorption and deabsorption on resins. In the case of *Ginkgo biloba* leaves, the extraction is performed with a mixture of ethanol and water.

Pesticides are not the only undesirable contaminants in *Ginkgo biloba* extracts: for example, EP 1 968 625 describes a multi-step preparation method of a *Ginkgo biloba* extract with a low content of 4'-O-methyl pyridoxine, also known as *ginkgo* toxin, and/or biflavones. In this case, however, the undesirable components are naturally present in the plant.

Finally, EP 1 868 626 discloses a method of preparing *Ginkgo biloba* extracts having a low content of polycyclic aromatic hydrocarbons deriving from the use of fossil fuels close to *Ginkgo* crops. The process described is highly complex, comprising eleven steps, long preparation times and the use of expensive reagents such as polyamides, or toxic reagents such as lead salts.

Practically all the known processes involve one or more steps of removal of the lipophilic components of the *Ginkgo* extract (in particular biflavones and ginkgols). Said extraction also reduces any lyophilic pesticide content present, while pesticides with higher polarity remain in the extract, as their behaviour is more similar to that of the hydrophilic components (such as flavone glycosides and terpenes).

There is consequently a need for a convenient purification method which reduces or eliminates pesticides or other pollutants from *Ginkgo biloba* leaf extracts in order to comply with the limits imposed by the legislation, especially in the USA, governing the residual content of any type of pesticide in products of plant origin for pharmaceutical, nutritional or cosmetic use.

DESCRIPTION OF THE INVENTION

It has now been found that the pesticide content of *Ginkgo biloba* extracts can be reduced by a process comprising:
a) liquid-liquid extraction of the extract to obtain a medium polarity fraction containing *ginkgo* terpenes and pesticides not removable with hexane, and a high polarity fraction containing *ginkgo* flavone glycosides;
b) crystallisation from the medium polarity fraction obtained at step a) to give an intermediate with a ginkgolide content of not less than 50%;
c) crystallisation from the residual solution obtained at step b) to give an intermediate with a bilobalide content of not less than 50%;
d) mixing of the high polarity fraction obtained at step a) with the *ginkgo* terpene intermediate and bilobalide intermediate obtained at steps b) and c).

The process of the invention, in addition to eliminating or substantially reducing the residual pesticide content, also allows the content of *ginkgo* terpenes and their relative ratio to be controlled.

The invention therefore also relates to extracts obtainable from the process described above, with a pre-determined ratio of *ginkgo* terpenes.

According to the invention, step a) produces one fraction enriched with *ginkgo* terpenes and one enriched with *ginkgo* flavone glycosides by extraction with a water-immiscible solvent selected from esters, chlorinated hydrocarbons, mixtures of hydrocarbons and alcohols, ketones and mixtures of ketones and alcohols, preferably a C2-C8 ester, such as ethyl acetate and t-butyl acetate or a toluene-butanol mixture.

The *ginkgo* terpenes are crystallised in water and C1-C5 alcohol mixtures, while the crystallisation from the terpene-rich fraction obtained at step c) is performed in water or a mixture of water and C1-C3 alcohols. The process according to the invention eliminates medium-polarity pesticides which are not removed with the ginkgols.

The invention is illustrated in greater detail in the examples below.

Example 1

Purification of the Extract Produced According to Example I in U.S. Pat. No. 5,700,468 and EP 0 360 556 (Indena)

1) 100 kg of chopped leaves is extracted 4 times with 400 l of 60% (w/w) acetone at a temperature of approx. 50° C.
2) The combined percolates are extracted in countercurrent with 500 l of hexane.
3) The defatted solution is concentrated under vacuum to a volume of 200 l, left overnight at 2° C., and then centrifuged to separate the biflavone fraction.
4) The aqueous solution is extracted in countercurrent with 400 l of an 8/2 v/v mixture of n-butanol/toluene.
5) The organic solution is concentrated under vacuum to a small volume, substituting with water. The concentrate is taken up with water to obtain a solution with approx. 30% of dry residue.
6) The solution is extracted in countercurrent with approx. 65 l of ethyl acetate. The aqueous phase is concentrated to a syrup-like consistency and dried under vacuum, to obtain an intermediate enriched with *ginkgo* flavone glycosides and devoid of terpenes (1.95 kg).

7) The ethyl acetic phase is concentrated under vacuum to a syrup-like consistency, and the residue is taken up with 3 l of 75% aqueous ethanol.

8) The solution is extracted in countercurrent with 20 l of hexane, eliminating the combined organic phases.

9) The water-alcohol solution is concentrated under vacuum to a syrup-like consistency, and 0.9 l of 50% aqueous ethanol is added.

The resulting solution is reflux heated under stirring, then cooled to room temperature and left to crystallise for 4 days.

10) The solution is then filtered and the solid washed with 50% EtOH and dried under vacuum, to obtain 95 g of purified ginkgolides.

11) The mother liquor is concentrated under vacuum to eliminate the ethanol, and the residue is then taken up with 1.9 l of water and heated to 90° C. under stirring for 30 minutes. The aqueous solution is separated, and the residue is taken up 3 more times with 1.9 l of water at 90° C., the aqueous solution being recovered every time.

12) The aqueous solutions are combined and extracted in countercurrent with 14 l of hexane.

13) The aqueous solution is concentrated to a volume of 0.3 l; 0.1 l of 95° EtOH is then added, and the solution is heated to 50° C. under stirring, then cooled to room temperature and left to crystallise for 3 days.

14) The solution is filtered and the solid is washed with 20% EtOH and dried under vacuum to obtain 103 g of purified bilobalide.

15) The products obtained in points 6, 10 and 14 are mixed to give 2.15 kg of *Ginkgo biloba* extract with the following characteristics: *ginkgo* flavone glycosides 26.0%; bilobalide 3.2%; ginkgolides 3.5%; ginkgolic acids <5.0 ppm; each pesticide <10 ppb.

Example 2

Purification of the Extract Produced as Described in Example II of U.S. Pat. No. 5,700,468, EP 0 360 556 (Indena)

1) 100 kg of chopped leaves is extracted 4 times with 400 l of 50% (w/w) methanol at the temperature of approx. 35° C.

2) The combined percolates are concentrated to 100 l under vacuum at 40° C., the concentrate is taken up with 100 l of methanol, and the suspension obtained is filtered.

3) The filtered solution is extracted 3 times with 100 l of a 9:2 mixture of toluene/n-butanol.

4) The combined organic phases are counterwashed with 50 l of 50% methanol.

5) The water-methanol solutions are concentrated under vacuum to an aqueous solution and, after filtration, are extracted with an 8:2 mixture of n-butanol/toluene.

6) The organic solution is counterwashed with water and concentrated under vacuum to a small volume, substituting with water. The solution is taken up with water to obtain a solution with a dry residue of 20%.

7) The resulting solution is extracted in countercurrent with 90 l of a 1:1 mixture of n-butanol/toluene. The aqueous phase is concentrated to a syrup-like consistency and dried under vacuum to obtain an intermediate enriched with *ginkgo* flavone glycosides and devoid of terpenes (2.05 kg).

8) The n-butanol/toluene mixture is concentrated under vacuum to a syrup-like consistency, and the residue is taken up with 3.5 l of 60% aqueous ethanol.

9) The resulting solution is extracted in countercurrent with 20 l of hexane, eliminating the combined organic phases.

10) The water-alcohol solution is concentrated under vacuum to a syrup-like consistency, and 1.2 l of 40% aqueous ethanol is added.

The resulting solution is reflux heated under stirring for 45 minutes, then cooled to room temperature and left to crystallise for 3-4 days.

11) The solution is then filtered and the solid washed with 40% EtOH and dried under vacuum, to obtain 97 g of purified ginkgolides.

12) The mother liquor is concentrated under vacuum to eliminate the ethanol, and the residue is then taken up with 2 l of water and heated at 90° C. under stirring for 30 minutes. The aqueous solution is separated, and the residue is taken up 3 more times with 2 l of water at 90° C., the aqueous solution being recovered every time.

13) The aqueous solutions are combined and extracted in countercurrent with 17 l of hexane.

14) The aqueous solutions are concentrated to a volume of 0.4 l, and 0.15 l of 95°EtOH is added; the resulting solution is heated at 50-55° C. under stirring for 30 minutes, then cooled to room temperature and left to crystallise for 3-4 days.

15) The solution is filtered and the solid is washed with 20% EtOH and dried under vacuum at 60° C. to obtain 110 g of purified bilobalide.

16) The products obtained in points 7, 11 and 15 are mixed to give 2.26 kg of *Ginkgo biloba* extract similar to that obtained in example 1.

Example 3

Purification of the Extract Produced According to Example I in EP 431 535 (Schwabe)

1) 100 kg of chopped leaves is extracted twice with 750 kg of 60% (w/w) acetone for 30 mins at the temperature of 57-59° C.

2) The combined extracts are concentrated to an aqueous solution with a dry residue of 30-40%, an equal volume of water is added, and the mixture is left under stirring for one hour at 12° C.

3) The alkylphenol-rich precipitate is separated by centrifugation and eliminated.

4) 30% of ammonium sulphate is added to the clarified solution under stirring, and the solution is extracted twice with half a volume of a 6:4 mixture of methyl ethyl ketone/acetone.

5) The combined methyl ethyl ketone/acetone solutions are concentrated under vacuum to a dry residue of 50-70%, and then diluted with water and 95% ethanol to obtain a 50% ethanol solution with a dry residue of 10%.

6) An aqueous solution of lead hydroxide acetate is added under stirring until the colour changes from brown to light brown. The precipitate obtained is eliminated by centrifugation.

7) The centrifuged solution is extracted 3 times with ⅓ volume of hexane.

8) The defatted solution is concentrated to an aqueous solution under vacuum, and 20% of ammonium sulphate is added and extracted twice with half a volume of a 6:4 mixture of methyl ethyl ketone/ethanol. The combined organic phases are washed with 20% of ammonium sulphate, removing any water and solid formed.

9) The clear solution is then concentrated under vacuum to a small volume, substituting with water.

The concentrate is taken up with water to obtain a solution with approx. 10% of dry residue.

10) The solution is extracted in countercurrent with approx. 100 l of t-butyl acetate. The aqueous phase is concentrated to a syrup-like consistency and dried under vacuum to obtain an intermediate enriched with *ginkgo* flavone glycosides and devoid of terpenes (1.88 kg).

11) The butyl acetic phase is concentrated under vacuum to a syrup-like consistency, and 0.8 l of 60% aqueous ethanol is added.

The resulting solution is reflux heated under stirring for 25 minutes, then cooled to room temperature and left to crystallise for 2 days.

12) The solution is then filtered and the solid washed with 60% EtOH and dried under vacuum, to obtain 98 g of purified ginkgolides.

13) The mother liquor is concentrated under vacuum to eliminate the ethanol, and the residue is then taken up with 1.9 l of water and heated at 90° C. under stirring for 30 minutes. The aqueous solution is separated, and the residue is taken up 3 more times with 1.9 l of water at 90° C., the aqueous solution being recovered every time.

14) The combined aqueous solutions are concentrated to a volume of 0.6 l and heated to 70° C., under stirring, for 60 minutes, then cooled to room temperature and left to crystallise for 1 day.

15) The resulting solution is filtered and the solid is washed with water and dried under vacuum to obtain 99 g of purified bilobalide.

16) The products obtained in points 10, 12 and 15 are mixed to give 2.08 kg of *Ginkgo biloba* extract similar to that obtained in example 1.

Example 4

Purification of Extract Produced According to JP 09110713 (Nippon Green Wave)

1) 100 kg of chopped *ginkgo* leaves is extracted 3 times with 500 l of 70% ethanol at 50° C. for 30 hours.

2) The combined percolates are concentrated to 100 l under vacuum and the concentrate is taken up with 100 l of water.

The suspension obtained is filtered.

3) The filtered solution is introduced into a chromatography column containing 100 l of HP20 resin (Mitsubishi) to adsorb the extract. The column is then washed with 200 l of water, and the extract is recovered by eluting with 200 l of 70% ethanol.

4) The water-ethanol solution is concentrated under vacuum to a small volume, substituting with water. The concentrate is taken up with 20% ethanol to obtain a solution with a dry residue of 20%.

5) The resulting solution is extracted in countercurrent with 70 l of methylene chloride. The water-ethanol phase is concentrated to a syrup-like consistency and dried under vacuum to obtain an intermediate enriched with *ginkgo* flavone glycosides and devoid of terpenes (2.4 kg).

6) The chloromethylene phase is concentrated under vacuum to a syrup-like consistency, and the residue is taken up with 4 l of 75% aqueous methanol.

7) The resulting solution is extracted 10 times with 2 l of hexane, eliminating the combined hexane phases.

8) The water-alcohol solution is concentrated under vacuum to a syrup-like consistency, and 1 l of 50% aqueous methanol is added.

The resulting solution is reflux heated under stirring for 30 minutes, then cooled to room temperature and left to crystallise for 5 days.

9) The solution is then filtered and the solid washed with 50% MeOH and dried under vacuum, to obtain 105 g of purified ginkgolides.

10) The mother liquor is concentrated under vacuum to eliminate the methanol, and the residue is then taken up with 2 l of water and heated at 90° C. under stirring for 30 minutes. The aqueous solution is separated, and the residue is taken up 3 more times with 2 l of water at 90° C., the aqueous solution being recovered every time.

11) The combined aqueous solutions are concentrated to a volume of 0.4 l, and 0.1 l of MeOH is added; the resulting solution is heated at 50° C. under stirring for 30 minutes, then cooled to room temperature and left to crystallise for 3 days.

12) The resulting solution is filtered and the solid is washed with 20% MeOH and dried under vacuum to obtain 102 g of purified bilobalide.

13) The products obtained in points 5, 9 and 12 are mixed to give 2.6 kg of *Ginkgo biloba* extract similar to that obtained in example 1.

Example 5

Purification of a Purified Extract Containing Pesticides with a High Terpene Content 1) 1 kg of *Ginkgo biloba* leaf extract containing 24% of *ginkgo* flavone glycosides, 12% of *ginkgo* terpenes, 2 ppm of ginkgolic acids and 315 ppb of chlorpyrifos and triciclazole is suspended under stirring in 5 l of water.

2) The suspension is extracted 12 times with 5 l of ethyl acetate at room temperature. The aqueous phase is then concentrated to a syrup-like consistency and dried under vacuum to obtain an intermediate enriched with *ginkgo* flavone glycosides and devoid of terpenes (810 g).

3) The combined ethyl acetic phases are concentrated under vacuum to a syrup-like consistency, and the residue is taken up with 2 l of 50% aqueous ethanol.

The resulting solution is reflux heated under stirring for 1 hour, then cooled to room temperature and left to crystallise for 2 days.

4) The solution is then filtered and the solid washed with 50% EtOH and dried under vacuum, to obtain 82 g of purified ginkgolides.

5) The mother liquor is concentrated under vacuum to eliminate the ethanol, and the residue is then taken up with 2 l of water and heated at 90° C. under stirring for 15 minutes. The aqueous solution is separated, and the residue is taken up a second time with 2 l of water at 90° C., the aqueous solution being recovered.

6) The aqueous solutions are combined and concentrated under vacuum to a syrup-like consistency; the residue is then taken up with 400 ml of 10% EtOH. The resulting solution is heated at 50° C. under stirring for 60 minutes, then cooled to room temperature and left to crystallise for 2 days.

7) The solution is filtered and the solid is washed with 10% EtOH and dried under vacuum to obtain 70 g of purified bilobalide.

8) 41 g of purified ginkgolides and 35 g of purified bilobalide are mixed with the product obtained in point 2 to give 885 g of *Ginkgo biloba* extract with the following characteristics: a. *ginkgo* flavone glycosides 27%; b. *ginkgo* terpenes 6.8%; c. ginkgolic acids 1.0 ppm; d. each pesticide <10 ppb.

The process described removes the pesticides and allows the terpene content of the *Ginkgo biloba* extracts to be controlled, adjusting it as required at the step when the purified intermediates are mixed. In practice, the 24/6 ratio (GFG/GT) considered ideal in the extracts often differs from the natural ratio encountered in the plants. For example, Chinese leaves often have a higher terpene content, and a *ginkgo* terpene titre reduction step is required to obtain conforming extracts.

The table below shows the pesticide contents of extracts obtained according to the procedures described above. Two tests were conducted for each example: the procedure disclosed in the patent was exactly followed in the first, and treatment of the terpene fraction was added in the second.

All the extracts were obtained from the same plant.

|  | Example 1-Ref. Indena patents US 5,700,468, EP 0 3600 556 B1; example I | | Example 2-Ref. Indena patents US 5,700,468, EP 0 3600 556 B1; example II | | Example 3-Ref. Schwabe patent EP 0 431 535 B1; example I | | Example 4-Ref. Nippon Green Wave patent J09110713 | |
|---|---|---|---|---|---|---|---|---|
|  | Before pesticide removal | After pesticide removal | Before pesticide removal | After pesticide removal | Before pesticide removal | After pesticide removal | Before Pesticide removal | After pesticide removal |
| Tricyclazole (ppb) | 85 | <10 | 55 | <10 | 63 | <10 | 212 | <10 |
| Acetamiprid (ppb) | 24 | <10 | 16 | <10 | 27 | <10 | 92 | <10 |
| Imidacloprid (ppb) | 48 | <10 | 37 | <10 | 45 | <10 | 175 | <10 |
| Phorate (ppb) | 33 | <10 | 28 | <10 | 26 | <10 | 84 | <10 |

The invention claimed is:

1. A process for removing pesticides from *Ginkgo biloba* extracts comprising, the following steps:
   a) subjecting said extracts to liquid-liquid extraction with a water-immiscible solvent selected from esters, chlorinated hydrocarbons, mixtures of hydrocarbons and alcohols, ketones and mixtures of ketones and alcohols, to obtain a fraction containing *ginkgo* terpenes and pesticides not removable with hexane, and a fraction containing *ginkgo* flavone glycosides;
   b) crystallizing the *ginkgo* terpenes in mixtures of water and $C_1$-$C_3$ alcohols from the fraction containing *ginkgo* terpenes and pesticides not removable with hexane obtained in step a) to obtain a ginkgolide intermediate with a ginkgolide content of not less than 50% w/w and a residual solution;
   c) crystallizing in water or in a mixture of water and $C_1$-$C_3$ alcohols the residual solution obtained in step b) to obtain a bilobalide intermediate with a bilobalide content of not less than 50% w/w;
   d) mixing the fraction containing *ginkgo* flavone glycosides obtained in step a) with the ginkgolide intermediate and the bilobalide intermediate obtained in steps b) and c);

thereby removing said pesticides from said *Ginkgo biloba* extracts.

2. The process as claimed in claim 1 wherein the solvent is an ester having 2 to 8 carbon atoms.

* * * * *